(12) United States Patent
Hitchcock et al.

(10) Patent No.: US 10,589,080 B2
(45) Date of Patent: Mar. 17, 2020

(54) DISINFECTING CAP FOR MALE LUERS

(71) Applicant: Merit Medical Systems, Inc., South Jordan, UT (US)

(72) Inventors: Robert Hitchcock, Salt Lake City, UT (US); Mahender Avula, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 47 days.

(21) Appl. No.: 15/979,213

(22) Filed: May 14, 2018

(65) Prior Publication Data
US 2018/0256881 A1 Sep. 13, 2018

Related U.S. Application Data

(63) Continuation of application No. PCT/US2016/062061, filed on Nov. 15, 2016.
(Continued)

(51) Int. Cl.
*A61M 39/16* (2006.01)
*A61L 2/18* (2006.01)
(Continued)

(52) U.S. Cl.
CPC ............ *A61M 39/162* (2013.01); *A61L 2/16* (2013.01); *A61L 2/18* (2013.01); *A61L 2/26* (2013.01);
(Continued)

(58) Field of Classification Search
CPC ..... A61L 2/16; A61L 2/18; A61L 2/26; A61L 2202/122; A61L 2202/24; A61M 5/32;
(Continued)

(56) References Cited

U.S. PATENT DOCUMENTS

| 1,744,026 A | 10/1926 | Baltzley |
| 1,868,200 A | 7/1932 | Freedman |

(Continued)

FOREIGN PATENT DOCUMENTS

| CN | 205549223 | 9/2016 |
| EP | 0229786 | 7/1987 |

(Continued)

OTHER PUBLICATIONS

International Search Report and Written Opinion dated Jun. 22, 2018 for PCT/US2018/014237.
(Continued)

*Primary Examiner* — Timothy C Cleveland
(74) *Attorney, Agent, or Firm* — Stoel Rives LLP

(57) ABSTRACT

A male-disinfecting cap is configured to couple with and apply an antiseptic agent to medical male luer-lock connector of the type including a post having a lumen. The cap includes a receiving portion which defines a chamber. The post of the male luer-lock connector is received into a single opening of the chamber. The receiving portion is configured to fit within the skirt of the male luer-lock connector when the post is received into the receiving portion. At least one vent is defined on the internal surface of the receiving portion and extends from the opening into the chamber, where an antiseptic is disposed. Protrusions on the external surface of the receiving portion engage helical threads of the internally helically threaded skirt. The male-disinfecting cap also includes a seal that prevents evaporation of the antiseptic agent in the chamber prior to use.

17 Claims, 13 Drawing Sheets

Section A-A

Related U.S. Application Data

(60) Provisional application No. 62/255,724, filed on Nov. 16, 2015.

(51) Int. Cl.
| | |
|---|---|
| *A61M 5/32* | (2006.01) |
| *A61M 39/20* | (2006.01) |
| *A61L 2/16* | (2006.01) |
| *B65D 41/02* | (2006.01) |
| *A61L 2/26* | (2006.01) |
| *A61M 5/31* | (2006.01) |

(52) U.S. Cl.
CPC .............. *A61M 5/32* (2013.01); *A61M 39/20* (2013.01); *B65D 41/02* (2013.01); *A61L 2202/122* (2013.01); *A61L 2202/24* (2013.01); *A61M 39/16* (2013.01); *A61M 2005/3104* (2013.01); *A61M 2039/205* (2013.01)

(58) Field of Classification Search
CPC .... A61M 39/16; A61M 39/162; A61M 39/20; A61M 2005/3104; A61M 2039/205; B65D 41/02
See application file for complete search history.

(56) References Cited

U.S. PATENT DOCUMENTS

| | | | |
|---|---|---|---|
| 2,356,969 A | 5/1942 | Blum |
| 2,299,037 A | 10/1942 | Saueressig |
| 2,351,804 A | 6/1944 | Blum |
| 3,315,830 A | 4/1967 | Flynn |
| 3,431,548 A | 3/1969 | Busler |
| 3,446,596 A | 5/1969 | Salivar et al. |
| 3,976,311 A | 8/1976 | Spendlove |
| 3,987,930 A | 10/1976 | Fuson |
| 4,121,727 A | 10/1978 | Robbins et al. |
| 4,232,677 A | 11/1980 | Leibinsohn |
| 4,299,330 A | 11/1981 | Walter |
| 4,324,239 A | 4/1982 | Gordon et al. |
| 4,334,551 A | 6/1982 | Pfister |
| 4,344,551 A | 6/1982 | Pfister |
| 4,340,052 A | 7/1982 | Dennehey et al. |
| 4,346,703 A | 8/1982 | Dennehey et al. |
| 4,354,490 A | 10/1982 | Rogers |
| 4,369,781 A | 1/1983 | Gilson et al. |
| 4,402,691 A | 9/1983 | Rosenthal et al. |
| 4,432,764 A | 2/1984 | Lopez |
| 4,432,766 A | 2/1984 | Bellotti et al. |
| 4,440,207 A | 4/1984 | Genatempo et al. |
| 4,450,624 A | 5/1984 | Collier |
| 4,572,373 A | 2/1986 | Johansson |
| 4,597,758 A | 7/1986 | Aalto et al. |
| 4,624,664 A | 11/1986 | Peluso et al. |
| 4,667,837 A | 5/1987 | Vitello et al. |
| 4,671,306 A | 6/1987 | Spector |
| 4,778,447 A | 10/1988 | Velde et al. |
| 4,798,303 A | 1/1989 | Arnold |
| 4,810,241 A | 3/1989 | Rogers |
| 4,838,875 A | 6/1989 | Somor |
| D303,631 S | 9/1989 | Demarest |
| D310,542 S | 9/1990 | Regnault |
| 4,991,629 A | 2/1991 | Ernesto et al. |
| 5,006,114 A | 4/1991 | Rogers et al. |
| 5,184,742 A | 2/1993 | Decaprio et al. |
| D333,788 S | 3/1993 | Geschwender |
| 5,190,534 A | 3/1993 | Kendell |
| 5,195,957 A | 3/1993 | Tollini |
| 5,205,821 A | 4/1993 | Kruger et al. |
| 5,242,425 A | 9/1993 | White et al. |
| D340,112 S | 10/1993 | Zeman |
| D341,227 S | 11/1993 | Lang et al. |
| 5,269,771 A | 12/1993 | Thomas et al. |
| 5,385,372 A | 1/1995 | Utterberg |
| 5,439,451 A | 8/1995 | Collinson et al. |
| 5,445,270 A | 8/1995 | Dratz |
| 5,451,113 A | 9/1995 | Lund et al. |
| 5,466,219 A | 11/1995 | Lynn et al. |
| 5,492,147 A | 2/1996 | Challender et al. |
| 5,536,258 A | 7/1996 | Folden |
| 5,554,135 A | 9/1996 | Menyhay |
| 5,620,427 A | 4/1997 | Werschmidt et al. |
| 5,694,978 A | 12/1997 | Heilmann et al. |
| 5,702,017 A | 12/1997 | Goncalves |
| 5,738,663 A | 4/1998 | Lopez |
| 5,792,120 A | 8/1998 | Menyhay |
| 5,894,015 A | 4/1999 | Rechtin |
| 5,951,519 A | 9/1999 | Utterberg |
| 5,954,657 A | 9/1999 | Rados |
| 5,954,957 A | 9/1999 | Chin-Loy et al. |
| 6,045,539 A | 4/2000 | Menyhay |
| 6,152,913 A | 11/2000 | Feith et al. |
| 6,171,287 B1 | 1/2001 | Lynn et al. |
| D456,668 S | 5/2002 | Tse |
| D468,015 S | 12/2002 | Horppu |
| D470,888 S | 2/2003 | Kuboshima |
| 6,523,686 B1 | 2/2003 | Bae |
| 6,932,795 B2 | 8/2005 | Lopez et al. |
| 6,960,191 B2 | 11/2005 | Howlett et al. |
| 7,014,169 B2 | 3/2006 | Newton et al. |
| 7,040,598 B2 | 5/2006 | Raybuck |
| 7,040,669 B2 | 5/2006 | Kenmotsu et al. |
| 7,198,611 B2 | 4/2007 | Connell et al. |
| D545,964 S | 7/2007 | Blanco |
| D547,446 S | 7/2007 | Racz et al. |
| D550,355 S | 9/2007 | Racz et al. |
| 7,282,186 B2 | 10/2007 | Lake, Jr. et al. |
| 7,316,669 B2 | 1/2008 | Ranalletta |
| D573,643 S | 7/2008 | Brigham et al. |
| D607,325 S | 1/2010 | Rogers et al. |
| 7,762,524 B2 | 7/2010 | Cawthon et al. |
| 7,762,988 B1 | 7/2010 | Vitello |
| 7,763,006 B2 | 7/2010 | Tennican |
| 7,780,794 B2 | 8/2010 | Rogers et al. |
| D632,574 S | 2/2011 | Huntington et al. |
| 7,922,701 B2 | 4/2011 | Buchman |
| D639,421 S | 6/2011 | Sano et al. |
| 7,985,302 B2 | 7/2011 | Rogers et al. |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,587 B2 | 7/2012 | Solomon et al. |
| 8,231,602 B2 | 7/2012 | Anderson et al. |
| 8,273,303 B2 | 9/2012 | Ferlic et al. |
| 8,328,767 B2 | 12/2012 | Solomon et al. |
| 8,343,112 B2 | 1/2013 | Solomon et al. |
| 8,419,713 B1 | 4/2013 | Solomon et al. |
| 8,523,830 B2 | 9/2013 | Solomon et al. |
| 8,523,831 B2 | 9/2013 | Solomon et al. |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,740,864 B2 | 6/2014 | Hoang |
| 8,784,388 B2 | 7/2014 | Charles et al. |
| 8,808,637 B2 | 8/2014 | Ferlic |
| 8,961,475 B2 | 2/2015 | Solomon et al. |
| 9,079,692 B2 | 7/2015 | Solomon et al. |
| 9,101,750 B2 | 8/2015 | Solomon et al. |
| 9,114,915 B2 | 8/2015 | Solomon et al. |
| 9,242,084 B2 | 1/2016 | Solomon et al. |
| 9,352,140 B2 | 5/2016 | Kerr et al. |
| 2002/0093192 A1 | 7/2002 | Matkovich |
| 2003/0140441 A1 | 7/2003 | Stafford |
| 2003/0153865 A1 | 8/2003 | Connell et al. |
| 2003/0181849 A1 | 9/2003 | Castellanos |
| 2003/0198502 A1 | 10/2003 | Maloney et al. |
| 2004/0039341 A1 | 2/2004 | Ranalletta |
| 2004/0195136 A1 | 10/2004 | Young et al. |
| 2004/0201216 A1 | 10/2004 | Segal et al. |
| 2004/0214316 A1 | 10/2004 | O'Connell |
| 2004/0258560 A1 | 12/2004 | Lake, Jr. et al. |
| 2005/0033267 A1 | 2/2005 | Decaria |

(56) References Cited

U.S. PATENT DOCUMENTS

| | | |
|---|---|---|
| 2005/0038397 A1 | 2/2005 | Newton et al. |
| 2005/0124970 A1 | 6/2005 | Kunin et al. |
| 2005/0147524 A1 | 7/2005 | Bousquet |
| 2005/0183971 A1 | 8/2005 | Petricca |
| 2005/0203460 A1 | 9/2005 | Kim |
| 2005/0245883 A1 | 11/2005 | Baldwin |
| 2005/0265773 A1 | 12/2005 | De Laforcade |
| 2005/0266714 A1 | 12/2005 | Higgins et al. |
| 2006/0030827 A1 | 2/2006 | Raulerson et al. |
| 2006/0177250 A1 | 8/2006 | Nakagaki |
| 2007/0112333 A1 | 5/2007 | Hoang et al. |
| 2007/0202177 A1 | 8/2007 | Hoang |
| 2007/0282280 A1 | 12/2007 | Tennican |
| 2007/0287989 A1 | 12/2007 | Crawford et al. |
| 2007/0293818 A1 | 12/2007 | Stout et al. |
| 2007/0293822 A1 | 12/2007 | Crawford et al. |
| 2008/0019889 A1 | 1/2008 | Rogers et al. |
| 2008/0021381 A1 | 1/2008 | Lurvey et al. |
| 2008/0027399 A1 | 1/2008 | Harding et al. |
| 2008/0033371 A1 | 2/2008 | Updefraff et al. |
| 2008/0038167 A1 | 2/2008 | Lynn |
| 2008/0039803 A1 | 2/2008 | Lynn |
| 2008/0097407 A1 | 2/2008 | Plishka |
| 2008/0086091 A1 | 4/2008 | Anderson et al. |
| 2008/0095680 A1 | 4/2008 | Steffens et al. |
| 2008/0105704 A1 | 5/2008 | Pritchard |
| 2008/0107564 A1 | 5/2008 | Sternberg et al. |
| 2008/0132880 A1 | 6/2008 | Buchman |
| 2008/0147047 A1 | 6/2008 | Davis et al. |
| 2008/0177250 A1 | 7/2008 | Howlett et al. |
| 2008/0190485 A1 | 8/2008 | Guala |
| 2008/0235888 A1 | 10/2008 | Vaillancourt et al. |
| 2009/0008393 A1 | 1/2009 | Howlett et al. |
| 2009/0062766 A1 | 3/2009 | Howlett et al. |
| 2009/0099529 A1 | 4/2009 | Anderson et al. |
| 2009/0149819 A1 | 6/2009 | Chelak |
| 2009/0205151 A1 | 8/2009 | Fisher et al. |
| 2010/0003067 A1 | 1/2010 | Shaw et al. |
| 2010/0047123 A1 | 2/2010 | Solomon et al. |
| 2010/0049170 A1 | 2/2010 | Solomon et al. |
| 2010/0063482 A1 | 3/2010 | Mansour et al. |
| 2010/0100056 A1 | 4/2010 | Cawthon et al. |
| 2010/0242993 A1 | 9/2010 | Hoang et al. |
| 2010/0306938 A1 | 12/2010 | Rogers et al. |
| 2010/0313366 A1 | 12/2010 | Rogers et al. |
| 2011/0044850 A1 | 2/2011 | Solomon et al. |
| 2011/0054440 A1 | 3/2011 | Lewis |
| 2011/0064512 A1 | 3/2011 | Shaw et al. |
| 2011/0165020 A1 | 7/2011 | Truggvason |
| 2011/0213341 A1 | 9/2011 | Solomon et al. |
| 2011/0217212 A1 | 9/2011 | Solomon et al. |
| 2011/0232020 A1 | 9/2011 | Rogers et al. |
| 2011/0277788 A1 | 11/2011 | Rogers et al. |
| 2011/0314619 A1 | 12/2011 | Schweikert |
| 2012/0016318 A1 | 1/2012 | Hoang et al. |
| 2012/0039764 A1 | 2/2012 | Solomon |
| 2012/0039765 A1 | 2/2012 | Solomon |
| 2012/0082977 A1 | 4/2012 | Rajagopal et al. |
| 2012/0216359 A1 | 8/2012 | Rogers et al. |
| 2013/0019421 A1 | 1/2013 | Rogers et al. |
| 2013/0072908 A1 | 3/2013 | Solomon et al. |
| 2013/0171030 A1 | 7/2013 | Ferlic et al. |
| 2013/0197485 A1 | 8/2013 | Gardner et al. |
| 2014/0010481 A1 | 1/2014 | Last et al. |
| 2014/0135739 A1 | 5/2014 | Solomon et al. |
| 2014/0227144 A1 | 8/2014 | Liu et al. |
| 2015/0231384 A1 | 8/2015 | Ma et al. |
| 2015/0273199 A1 | 10/2015 | Adams et al. |
| 2015/0374968 A1 | 12/2015 | Solomon et al. |
| 2016/0038701 A1 | 2/2016 | White et al. |
| 2016/0045629 A1 | 2/2016 | Gardner et al. |
| 2016/0106968 A1 | 4/2016 | Solomon et al. |
| 2017/0245618 A1 | 8/2017 | Chen et al. |
| 2019/0099593 A1 | 4/2019 | Avula et al. |
| 2019/0209781 A1 | 7/2019 | Solomon et al. |

FOREIGN PATENT DOCUMENTS

| | | |
|---|---|---|
| EP | 0462355 | 12/1991 |
| JP | 64002760 | 1/1989 |
| WO | 2004035245 | 4/2004 |
| WO | 2006099306 A2 | 9/2006 |
| WO | 2008089196 A2 | 7/2008 |
| WO | 2008100950 A2 | 8/2008 |
| WO | 2010002808 A1 | 1/2010 |
| WO | 2010141508 A1 | 12/2010 |
| WO | 2011141508 | 12/2010 |
| WO | 2011053924 A1 | 5/2011 |
| WO | 2011066565 A1 | 6/2011 |
| WO | 2011066586 A1 | 6/2011 |
| WO | 2013184716 | 12/2013 |
| WO | 2015174953 | 11/2015 |

OTHER PUBLICATIONS

Office Action dated May 25, 2018 for U.S. Appl. No. 15/203,002.
Office Action dated Jun. 7, 2018 for U.S. Appl. No. 14/947,241.
International Search Report and Written Opinion dated Jan. 24, 2019 for PCT/US2018/054202.
European Search Report dated Mar. 6, 2012 for EP08727689.5.
European Search Report dated Jun. 20, 2017 for EP10827614.8.
International Search Report and the Written Opinion dated Jan. 26, 2011 for PCT/US2010/058404.
International Search Report and Written Opinion dated Jan. 6, 2011 for PCT/US2010/054995.
International Search Report and Written Opinion dated Feb. 7, 2011 for PCT/US2010/058453.
International Search Report and Written Opinion dated Aug. 1, 2008 for PCT/US2008/051087.
International Search Report with Written Opinion dated Aug. 31, 2009 for PCT/US2009/049094.
Notice of Allowance dated Jun. 7, 2017 for U.S. Appl. No. 14/162,207.
Notice of Allowance dated Sep. 1, 2017 for U.S. Appl. No. 14/162,207.
Office Action dated Jan. 27, 2010 for U.S. Appl. No. 12/014,388.
Office Action dated Feb. 27, 2018 for U.S. Appl. No. 14/978,925.
Office Action dated Apr. 4, 2018 for U.S. Appl. No. 14/845,004.
Office Action dated Apr. 22, 2011 for U.S. Appl. No. 12/164,310.
Office Action dated Apr. 26, 2018 for U.S. Appl. No. 14/797,533.
Office Action dated May 5, 2009 for U.S. Appl. No. 12/014,388.
Office Action dated Jun. 9, 2011 for U.S. Appl. No. 12/171,997.
Office Action dated Jun. 21, 2010 for U.S. Appl. No. 12/014,388.
Office Action dated Aug. 16, 2010 for U.S. Appl. No. 12/164,310.
Office Action dated Oct. 20, 2017 for U.S. Appl. No. 15/203,002.
Office Action dated Nov. 17, 2017 for U.S. Appl. No. 14/845,004.
Office Action dated Dec. 23, 2010 for U.S. Appl. No. 12/014,388.
Baxa Corporation Launches PadLock Set Saver for IV Safety press release, 2 pages, available at http://www.pr.com/press-release/55432. ,Oct. 10, 2007.
Baxa Corporation Padlock catalog, 3 pages, copyright 2009, available at http://www.baxa.com/SearchResults/ProductDetail/?id=6452BFB9-3048-7B87-701697FB93902BA6.
Baxa Corporation Padlock Microbial Testing Technical Paper, copyright 2007, 4 pages, available at http://www.baxa.com/resources/docs/technicalPapers/PadLockMicrobialChallengeTechPaper.pdf.
Baxa Corporation PadLock Set Saver Specifications and Instructions for Use, copyright 2007, 2 pages, available at http://www.baxa.com/resources/docs/5300103905C.pdf.
BD Q-Syte Luer Access Split Septum product brochure, 4 pages, available at http://www.bd.com/infusion/pdfs/D16333.pdf. ,Nov. 2008.
Braun product catalog, 2 pages. ,Aug. 2008.
Curos Port Protector, web page from http://www.iveramed.com/ ,Jul. 11, 2008.
Curos Port Protector product brochure, 2 pages, available at http://www.iveramed.com/clocs/Curos%20Brochure-FINAL.pdf. ,Nov. 2008.
Hospira Male/Female Sterile Cap product packaging insert and brochure, 2 pages. ,Aug. 2004.
Kippmed Vented Non-Vented Female Luer Lock Caps, The KippGroup, ,Jan. 1995 ,2 pgs.

(56) References Cited

OTHER PUBLICATIONS

Tego Connector product brochure, 2 pages, available at http://www.icumed.com/Docs-Tego/M1-1148%20TEG0%20Folder%20Brochure%20Rev.3.pdf. ,Nov. 2008.

Unomedical Medical Products catalog, 2 pages, available at http://www.unomedical.net/au/section05/section10/LocalSSI/..%5C..%5Cpdf%5Cmedical.pdf ,Jan. 2006.

Buchman, et al., A New Central Venous Catheter Cap: Decreased Microbial Growth and Risk for Catheter-Related Bloodstream Infection, The Journal of Vascular Access ,2009 ,11-21.

Maki, et al., In Vitro Studies of a Novel Antimicrobial Luer-Activated Needleless Connector for Prevention of Catheter-Related Blookstream Infection, Clinical Infection Diseases, vol. 50, Issue 12 ,Jun. 15, 2010 ,1580-1587.

Menyhay, et al., Disinfection of Needleless Catheter Connecors and Access Ports with Alcohol May Not Prevent Microbial Entry: The Promise of a Novel Antiseptic-Barrier Cap, Infection control and Hospital Epidemiology, vol. 27 No. 1 ,Jan. 2006 ,23-27.

Stoker, et al., One Less Problem, Safe Practrices when Administering IV Therapy, Managing Infection Control, 4 pgs ,Jun. 2008.

International Search Report and Written Opinion dated Feb. 1, 2017 for PCT/US2016/062061.

Office Action dated Mar. 27, 2019 for U.S. Appl. No. 14/797,533.

Notice of Allowance dated Sep. 17, 2018 for U.S. Appl. No. 14/845,004.

Notice of Allowance dated Oct. 25, 2018 for U.S. Appl. No. 14/947,341.

Notice of Allowance dated Nov. 9, 2018 for U.S. Appl. No. 15/203,002.

Office Action dated Sep. 14, 2018 for U.S. Appl. No. 14/978,925.

Office Action dated Nov. 29, 2018 for U.S. Appl. No. 14/797,533.

European Search Report dated Jun. 13, 2019 for EP16866954.7.

Office Action dated Jun. 3, 2019 for U.S. Appl. No. 14/978,925.

Office Action dated Jul. 17, 2019 for U.S. Appl. No. 14/797,533.

Section A-A

US 10,589,080 B2

DISINFECTING CAP FOR MALE LUERS

RELATED APPLICATIONS

This application is a continuation of International Application No. PCT/US2016/062061 filed on Nov. 15, 2016 which claims the benefit of U.S. Provisional Application No. 62/255,724 filed Nov. 16, 2015, the entire contents of each of which are hereby incorporated by reference.

TECHNICAL FIELD

The present invention relates to caps for medical connectors, and more particularly to caps that can be used to protect the sterility of unconnected male luer connectors, such as male luer connectors that may be used for fluid flow or for fluid delivery systems.

SUMMARY OF THE EMBODIMENTS

Disclosed herein are disinfecting caps, and related systems and methods, that can reduce the threat of microorganisms entering the bloodstream of a patient via fluid flow or fluid delivery systems, such as, for example, needleless injection sites and/or fluid transfer devices having an elongated male portion or male protrusion, such as, for example, a male luer. The disinfecting caps have vents that reduce the time of exposure of the male luer to disinfectant.

In a first embodiment of the invention there is provided a male-disinfecting cap configured to couple with and apply an antiseptic agent to medical male luer-lock connector of the type including a post having a lumen. The male luer-lock connector also has an internally helically threaded skirt surrounding the post. The cap includes a receiving portion which defines a chamber. The post of the male luer-lock connector is received into a single opening of the chamber. The receiving portion is configured to fit within the skirt of the male luer-lock connector when the post is received into the receiving portion. The receiving portion has an internal surface and an external surface. At least one vent is defined on the internal surface of the receiving portion and extends from the opening into the chamber, where an antiseptic is disposed. Protrusions on the external surface of the receiving portion engage helical threads of the internally helically threaded skirt. The male-disinfecting cap also includes a seal that prevents evaporation of the antiseptic agent in the chamber prior to use.

In another embodiment, a method of disinfecting a male luer-lock connector of the type having a post with a lumen through which fluid flows and an internally helically threaded skirt surrounding the post includes providing a male-disinfecting cap. The male-disinfecting cap has a receiving portion defining a chamber into which the post of the male luer-lock connector can be received. The chamber has a single opening. The receiving portion has an external surface and is configured to fit within the skirt of the male luer-lock connector when the post is received into the receiving portion. The internal surface defines at least one vent. The vent extends from the opening into the chamber. An antiseptic agent is disposed in the chamber. The method includes engaging protrusions on the external surface of the receiving portion with helical threads of the internally helically threaded skirt. The method also includes undoing a seal which prevents evaporation of the antiseptic agent in the chamber prior to use so as to permit the opening to receive the post. The method also moves the cap in relation to the male luer-lock connector so that the antiseptic agent comes into contact with the post.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Definitions. As used in this description and the accompanying claims, the following terms shall have the meanings indicated, unless the context otherwise requires:

"NIS"—Needleless Injection Site (sometimes called LAV).

"LAV"—Luer Access Valve (also called NIS). A "LAV" is supposed to be made in conformity with industry standards for a luer. A NIS may be made in conformance with industry standards for a luer, but may not be; instead the NIS may be made in conformance with a manufacturer-specific, non-industry-standard specification.

A male connector to be disinfected by the present invention may be designed for use with a NIS, or more particularly for use with a LAV.

The terms "proximal" and "distal," when used herein relative to a cap, are such that an NIS or LAV is inserted into a proximal end of the cap and advanced toward a distal end of the cap.

In illustrative embodiments, a male-disinfecting cap has vents which allow for faster evaporation of disinfectant inside the cap. Specifically, the male-disinfecting caps frequently have disinfectant inside of them, and a seal on an exterior surface which prevents evaporation of the disinfectant. When the cap is mated with a male connector, the seal must be removed. Because of the tight fit in a luer-fit connection, the disinfectant within the cap evaporates slowly, if at all. Illustrative embodiments of the invention have vents which provide faster evaporation of the disinfectant.

Figure 1:
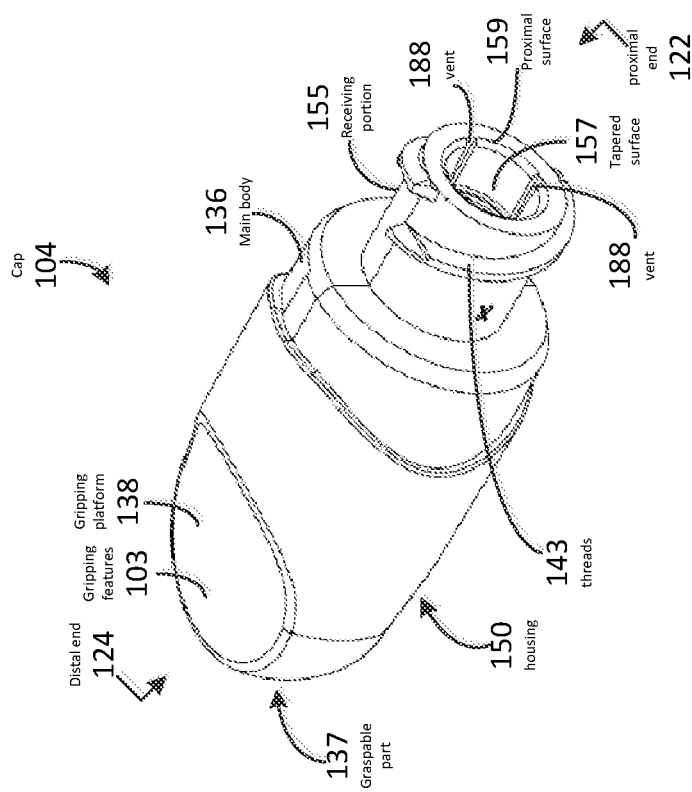
FIG. 1 is a perspective view of the housing component of an embodiment of the invention.

FIGS. 1-5 show a housing component of an embodiment of the invention. FIG. 1 is a perspective view of the housing component 150 of an embodiment of the invention. The housing 150 can extend between a closed distal end 124 and an open proximal end 122. The closed distal end 124 does not permit any fluid flow there through and serves as a barrier between an interior of the housing 150 and an exterior environment. The open proximal end 122 of the housing 150 is configured to receive at least a portion of a male luer tip. Although the proximal end 122 is referred to as open, it should be understood that such open proximal end 122 may be sealed prior to use, as known by those in the art.

The cap 104 defines an extension, elongated portion, receiving portion or projection 155 that extends proximally from the main body 136 of the cap housing 150. The receiving portion 155 is configured to couple with a medical connector that includes a male protrusion. The male luer passes through an opening formed by a proximal surface 159 of the receiving portion 155 and couples with the cap 104. The receiving portion 155 includes a connection interface that is configured to effect the coupling. In the illustrated embodiment, the receiving portion 155 is substantially cylindrical, and the connection interface comprises one or more threads 143 that are positioned at an outwardly facing surface of the cylinder. Any other suitable connection interface is possible. Those having skill in the art will know how to size the receiving portion 155 to accept industry standard male luer connectors. A person having skill in the art would also know how to size threads 143 for corresponding threading engagement between the external threads 143 of the cap 104 and the internal threads of a skirt of a male connector.

The housing 150 may have a graspable part 137. The graspable part 137 can assist a user by providing a surface to which torque can be applied for threading engagement and disengagement of the cap 104 to a male luer. The graspable part 137 be an extension of the body 136 and may be positioned at the distal end 124 of the cap 104. The graspable part 137 can comprise any suitable gripping features 103, which in illustrated embodiments comprise opposing gripping regions or grasping platforms 138 that are configured to provide a convenient surface against which a user can press so as to hold and/or twist the cap 104.

The receiving portion 155 of the cap 104 has a vent 188 or a plurality of vents 188. These vents 188 allow for faster evaporation of disinfectant while the cap 104 is connected with a male connector than do traditional male caps. The vents 188 comprise channels that run along at least part of the tapered surface 157 of the receiving portion 155. Those having skill in the art will understand that the number of vents 188 is not limited to the number herein described. Some embodiments have a single vent 188. Other embodiments have more than one vent 188. For example, some embodiments have one, four or eight vents 188. Vents 188 may be straight or angled. The vents 188 may have different dimensions and/or angles. In a first preferred embodiment as shown, the vents 188 are straight. In this embodiment, there are four vents 188 spaced equidistantly around the tapered surface 157 of the receiving portion 155. The vents 188 run from the proximal end 122 of the receiving portion 155 towards a chamber inside the housing 150.

Figure 2:
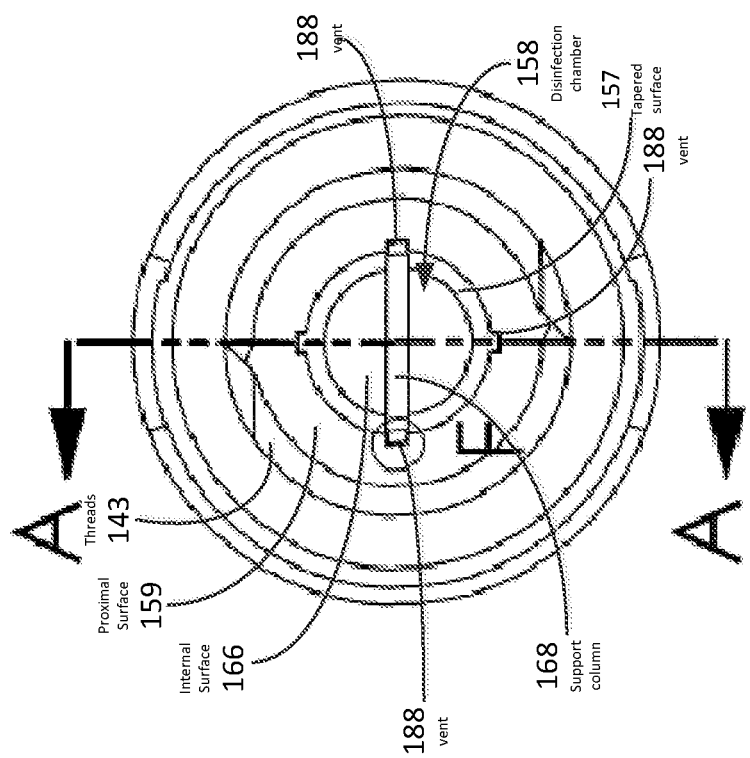
FIG. 2 is a proximal end view of the embodiment of FIG. 1.

FIG. 2 is a proximal end 122 view of the embodiment of FIG. 1. An internal surface 166 of the body region 136 can define a disinfection chamber 158, which can extend from the proximal end of the receiving portion 155 (i.e., the open proximal end of the cap 104) to the base wall 154. A proximal portion of the disinfection chamber 158 can include a proximal surface 159, which can be configured to form a fluid-tight seal with a seal on the receiving portion of the cap 104.

Generally, the male luer tip of a medical connector forms a fluid-tight seal with the receiving portion 155 of the cap 104 when the two are engaged. This fluid-tight seal is formed in the sense that fluid is not generally able to flow around the luer tip to the atmosphere (i.e., the ambient pressure outside of the cap). At least part of the interior of the receiving portion 155 may be shaped complementarily to an outer surface of a male luer tip of a medical connector with which the male cap 104 is configured to be used. For example, the interior of the receiving portion 155 may form a substantially frustoconical tapered surface 157 that complies with ISO luer standards, such that a portion of a male luer can form a seal. The frustoconical tapered surface 157 is preferably tapered so as to decrease in diameter in the distal direction. In some embodiments, the vents 188 may be cut into the frustoconical tapered surface 157 of the receiving portion 155.

Figure 3:
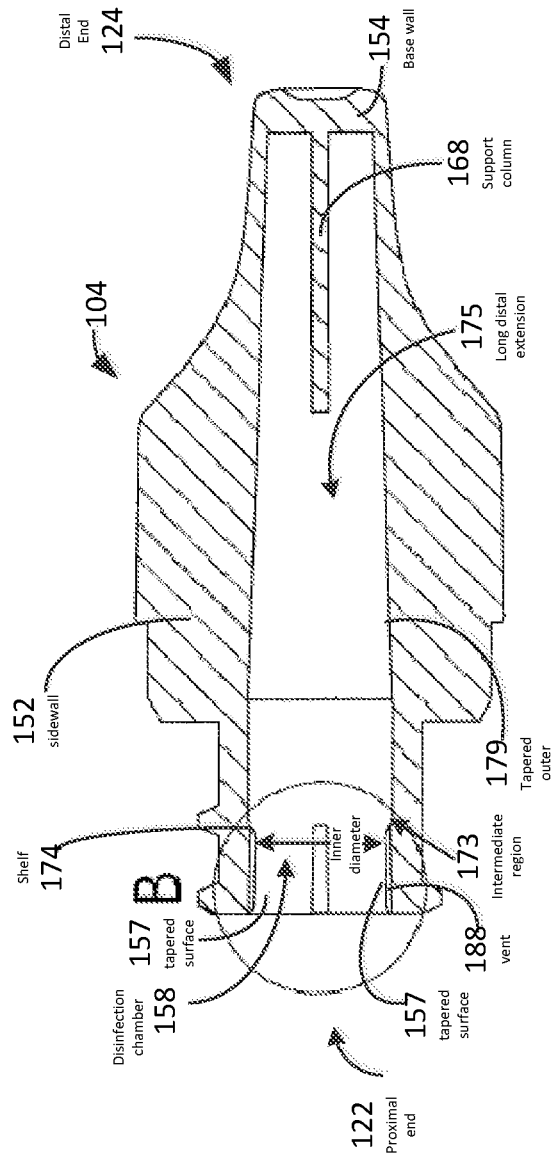
FIG. 3 is a sectional view taken along line A-A of FIG. 2.

FIG. 3 shows a sectional view taken along line A-A of FIG. 2. This cross-section is taken along a plane that runs precisely through two oppositely placed vents 188. The disinfection chamber 158 can further include an intermediate region 173. In the illustrated embodiment, the intermediate region 173 is formed by a rim, ridge, lip, or shelf 174, which is defined by a short, substantially frustoconical portion of the sidewall 152 that increases in diameter in the distal direction. The intermediate region 173 may interact with a movable member (discussed below).

After the intermediate region 173, the tapered surface 157 is formed towards the proximal end. The inner diameter formed between the tapered surface 157 widens towards the proximal end 122. The inner diameter is at its narrowest right along the interface of the intermediate region 173. As can be seen, in some embodiments, the vent 188 runs along the entire length of the tapered surface 157. Each vent 188 provides a channel through which disinfectant inside the cap 104 can communicate with the external atmosphere when the cap and the male luer are engaged.

Figure 4:
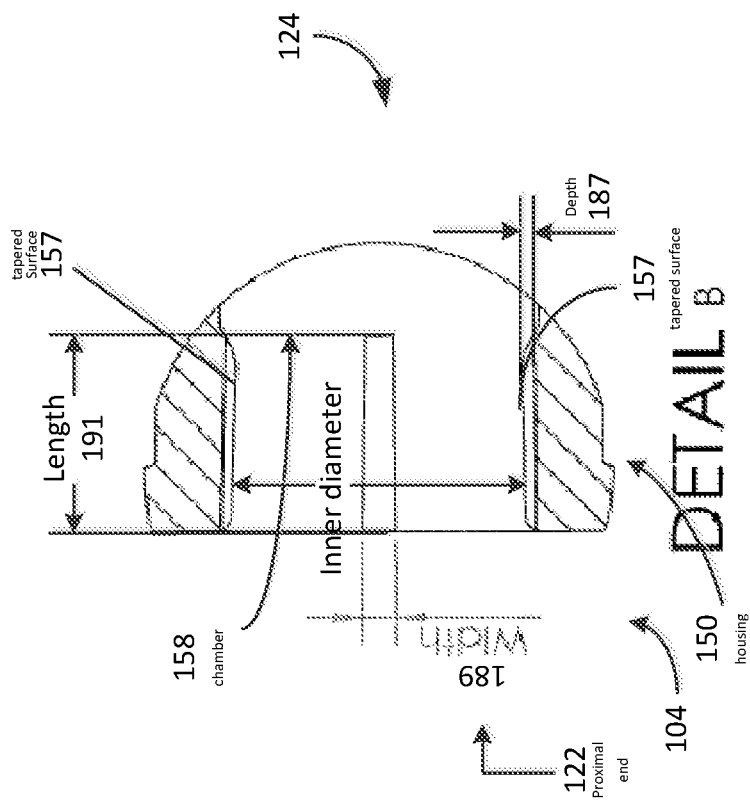
FIG. 4 is a detail of FIG. 3.
Figure 5:
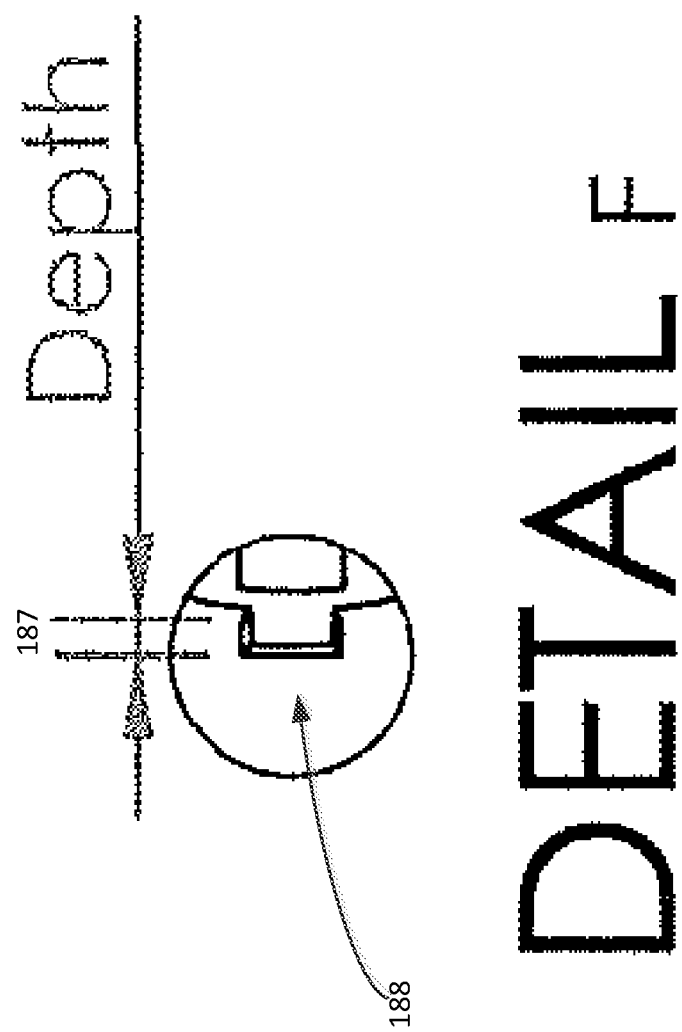
FIG. 5 is a detail of FIG. 2.

FIGS. 4 and 5 show details of an illustrative embodiment of straight vents 188 on the inner surface of the sidewalls of the housing 150. The vents 188 lead from the cap's 104 opening into the inner chamber 158 of the cap 104. FIG. 4, specifically, shows a detail of the illustrative embodiment shown in FIG. 3. Each vent 188 has a width 189, a depth 187 and a length 191. These dimensions are relative to the tapered surface 157 of the receiving region 155. In a preferred embodiment, each vent 188 has identical dimensions. In another preferred embodiment, each vent 188 has the same width 189. In another preferred embodiment, each vent 188 has the same depth 187. In another preferred embodiment, each vent 188 has the same length 191. The straight vents 188 preferably have a width 189 of 0.020" and a depth 187 of 0.010". In some embodiments, the straight vents 188 have consistent width 189 and depth 187 along their entirety. However, in some embodiments, the straight vents 188 have tapered widths 187 and tapered depths 189. Accordingly, the vents 188 are not required to have consistent dimensions throughout their entirety. For example, the width 189 of the vent 188 may increase towards the proximal end 122 of the cap 104. Male luer connectors generally have precise taper dimensions. For that reason, the inner diameter formed by the tapered surface 157 fits to the taper of the male luer connector and becomes smaller as it approaches the distal end 124 of the cap 104. The width 189 may vary proportionally along the tapered surface 157 as the size of the inner diameter varies. However, in some other embodiments, the width 189 may be consistent throughout the entirety of the vent 188.

In a similar manner, the depth 187 of the vent 188 does not have to be consistent throughout the entirety of the vent 188. For example, the depth 187 of the vent 188 may increase towards the distal end 124. The increase in the depth 187 may be proportional to the decrease of the inner diameter. For example, the inner diameter formed by the tapered surface 157 tapers towards the distal end to meet conventional ISO luer standards. In some embodiments, the increase in depth 187 of the vent 188 towards the distal end 124 may be exactly the same as the decrease of the size of the inner diameter towards the distal end 124.

Those skilled in the art will understand that the depth 187, width 189 and length 191 are variable. Furthermore, the size of the depth 187 and the width 189 may be inversely proportional. As the depth 187 increases the width 189 may be proportionately decreased. The vents 188 allow for faster evaporation of gaseous particles of the disinfectant within the cap 104 than caps without vents. In some embodiments, the vents 188 may be sized sufficiently so that liquid disinfectant is able to flow through the vents 188.

FIG. 5 shows a detail of FIG. 2. The view shows a proximal end 122 view of a vent 188. The vent 188 channel is shown recessed into the tapered surface. It should be understood that vents 188 may, but do not have to be, recessed completely through the tapered surface. As explained above, vent 188 may have a consistent depth 187. In some embodiments, the vent 188 may taper at the same angle as the tapered surface. Accordingly, the taper of the vent 188 may be seen in a proximal view of the vent 188.

It should be understood that although specific dimensions have been provided, other dimensions may be used. Different vent 188 dimensions cause different rates of evaporation. The longer and narrower the vent is, the slower the rate of evaporation and the less likely that airborne contaminants will make it into the chamber. In some embodiments, the vents may be configured so that substantial evaporation may have occurred 1.5 hours after engagement with a male connector.

FIGS. 6-10 show the housing component of an alternative embodiment of the invention. The cap 106 is the same as cap 104 except for the vents 288 inside the engagement region 155. The vents 288 shown in FIGS. 6-10 are angled. In a preferred embodiment, the vents 288 are helical. There may be one or more angled vents 288 within the cap 106. In caps 106 using the helical vents 288, the angle of the helix may be varied—which changes the length of the vents 288. Accordingly, the angle of the helix can be adjusted to vary the rate of evaporation. In addition to affecting the rate of evaporation, the vent 228 dimensions also affect the resistance to airborne contaminants passing into the chamber. The longer and narrower the vent 288 is, the slower the rate of evaporation and the less likely that airborne contaminants will make it into the chamber.

Figure 6:
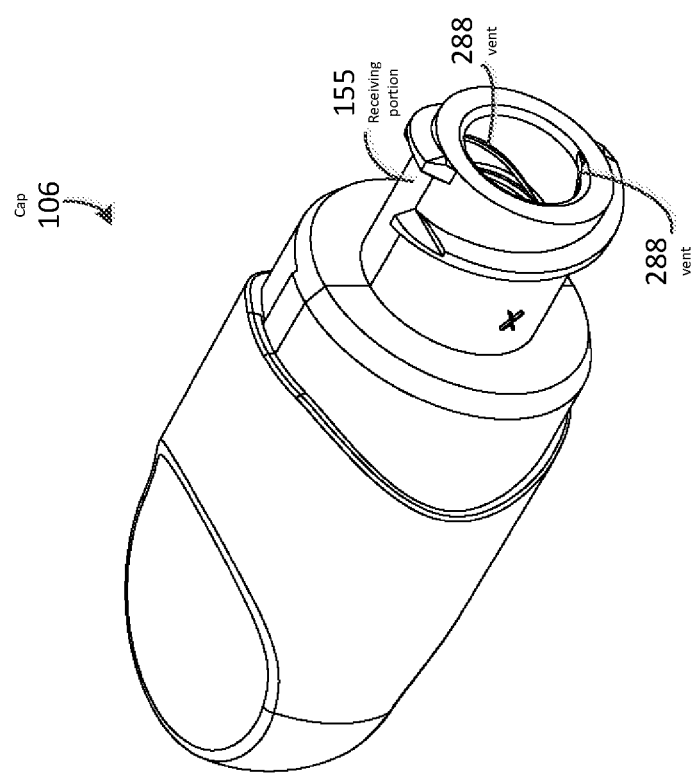
FIG. 6 is a perspective view of the housing component of an alternative embodiment of the invention.
Figure 7:
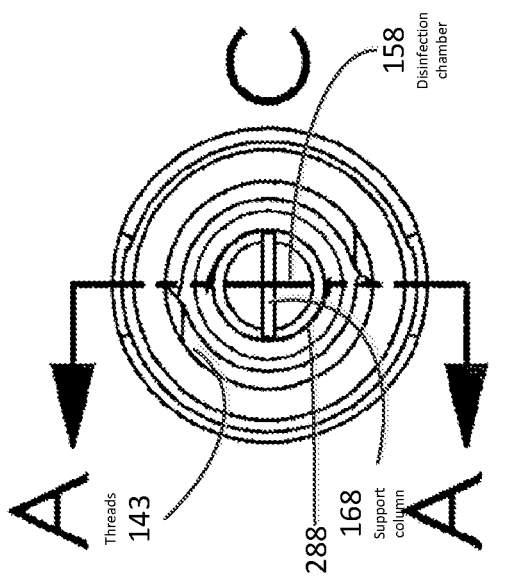
FIG. 7 is a proximal end view of the embodiment of FIG. 6.

FIG. 7 is a proximal end view of the embodiment of FIG. 6. A proximal view of the cap 106 shows the angled vents 288. Depending on the angle and the length, the vents 288 may run for a number of degrees. For example, the vent channel 288 may run 180 degrees or 360 degrees around the inner surface of the engagement region 155. As described in regards to straight vents 188, angled vents 288 similarly have a width, a length and a depth. The dimensions of the vents can be changed to effect evaporation.

Figure 8:
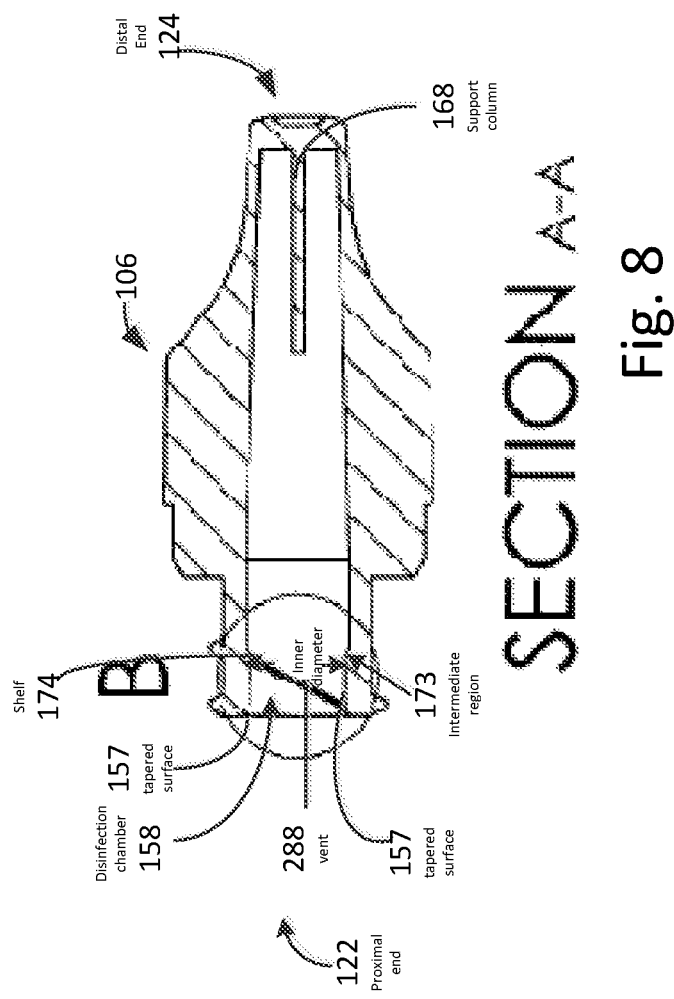
FIG. 8 is a sectional view taken along line A-A of FIG. 7.

FIG. 8 is a sectional view taken along line A-A of FIG. 7. The vent 288 allows for evaporation of disinfectant inside the cap 106, when the cap is engaged with a male connector. The vent 288 can begin at the opening of the cap near the proximal end 122. In some embodiments, the vent 288 may extend to the intermediate region 173. In some other embodiments, the vent 288 may extend beyond the intermediate region 173 and further into the chamber 158.

Figure 9:
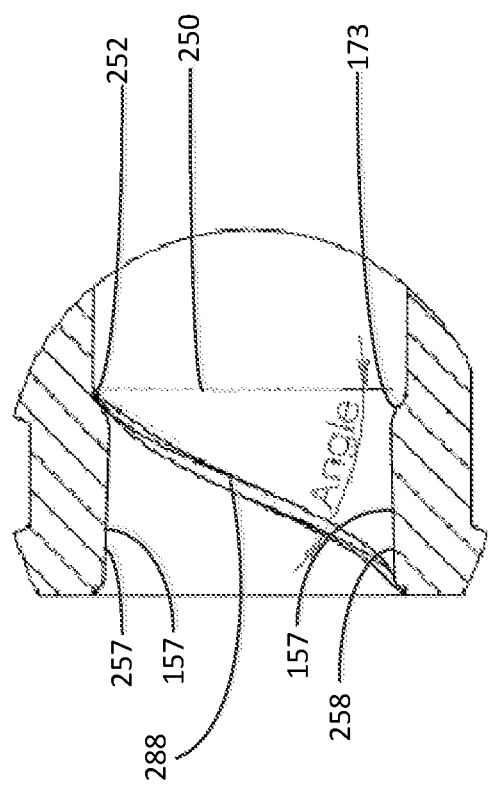
FIG. 9 is a detail of FIG. 8.

FIG. 9 shows a detail of FIG. 8. As discussed above, different angles will provide different lengths for the vent 288. The vent 288 may run from the open end of the cap to the intermediate region 173. In the illustrated embodiment, the vent 288 runs for 180 degrees. For example, the vent 288 runs from one opposing end 257 of the inside surface 157 to another opposing 258 of the inside surface 157. The vent 288 forms an angle A with a perpendicular axis 250 that slices through the distal part of the intermediate region 252.

Similar to the straight vents 288, each angled vent 288 has a width, a depth and a length. These dimensions are relative to the tapered surface 157 of the receiving region 155. In a preferred embodiment, each vent 288 has identical dimensions. In another preferred embodiment, each vent 288 has the same width. In another preferred embodiment, each vent 288 has the same depth. In another preferred embodiment, each vent 288 has the same length. The angled vents 288 preferably have a width of 0.020" and a depth of 0.010". In some embodiments, the angled vents 288 have consistent width and depth along their entirety. However, in some embodiments, the angled vents 288 have tapered widths and tapered depths. Accordingly, the vents 288 are not required to have consistent dimensions throughout their entirety. For example, the width of the vent 288 may increase towards the proximal end 122 of the cap 106. Male luer connectors generally have precise taper dimensions. For that reason, the inner diameter formed by the tapered surface 157 fits to the taper of the male luer connector and becomes smaller as it approaches the distal end 124 of the cap 104. The width may vary proportionally along the tapered surface 157 as the size of the inner diameter varies. However, in some other embodiments, the width may be consistent throughout the entirety of the vent 288.

Figure 10:
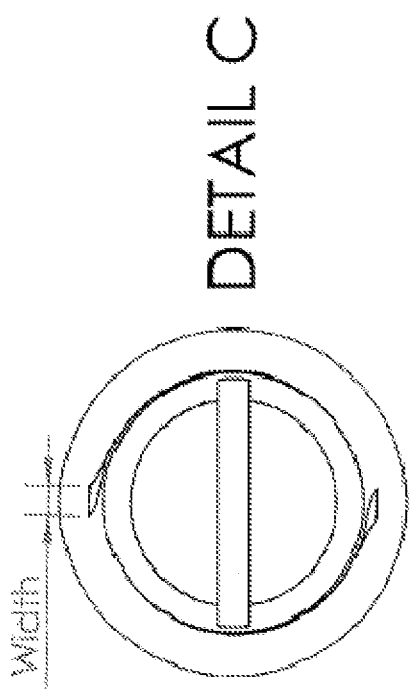
FIG. 10 is a detail of FIG. 7.

The length of the vent 288 is affected by the angle A. If the angle A increases, than the vent 288 length becomes shorter. If the angle A decreases, than the vent 288 length becomes longer. FIG. 10 is a detail of FIG. 7. FIGS. 9 and 10 show details of the helical vents 288 on the inner surface of the sidewalls of the housing 150. The vents lead from the cap's 106 opening into the inner chamber 158 of the cap 106.

Figure 11:
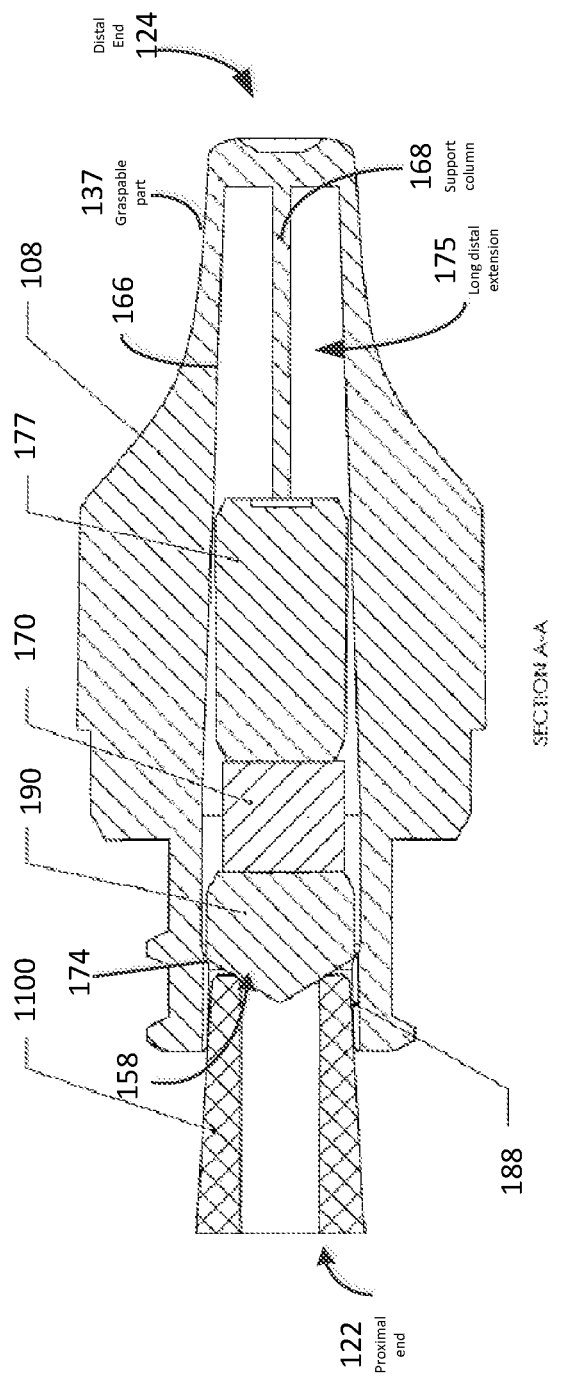
FIGS. 11-13 show a male luer being inserted into a cap having the housing of FIGS. 1-5.
Figure 12:
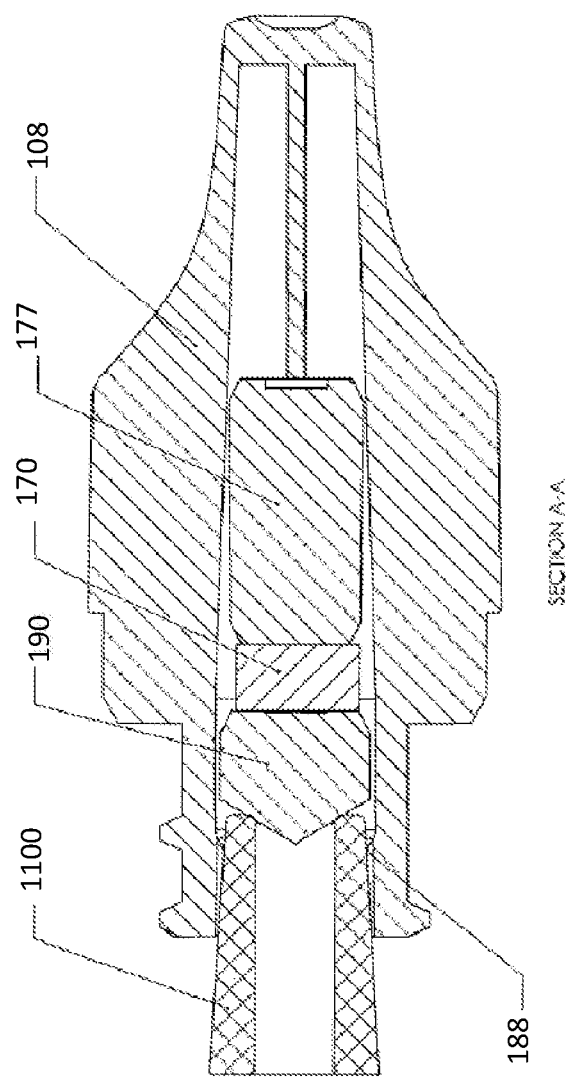
Figure 13:
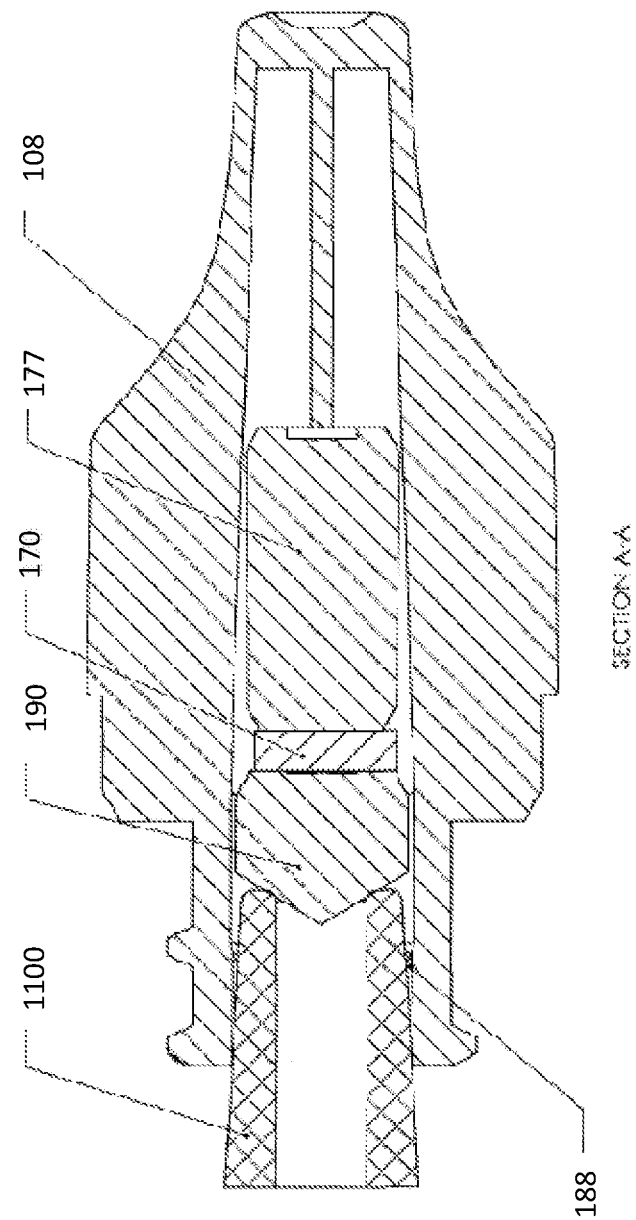

FIGS. 11-13 show a male luer 1100 being inserted into a cap 108, with FIG. 11 showing the luer first entering the cap's 108 opening and coming into contact with the movable member 190. The proximal face of the movable member 190 is shaped so it protrudes into the luer's 1100 opening and so that flow of antiseptic agent into the luer's cannula is inhibited. Similar to the cap shown in FIGS. 66A-66D of U.S. Pat. No. 8,231,587 to Solomon et al. (which patent is incorporated herein by reference) also includes a foam component 170 (which can hold an antiseptic agent, such as isopropyl alcohol, within its interstices) and a rod component 177 (which can provide a biasing force against the other internal cap components as well as the luer being inserted into the cap's opening). Straight vents 188, like those shown in the cap housing of FIGS. 1-6, are disposed around the inner circumference of the cap's 108 chamber 158, extending from the cap's 108 opening into the chamber 158.

An outer edge of a proximal surface of the movable member 190 can define a greater outer diameter than a minimum inner diameter of the shelf 174 such that the shelf 174 can maintain the movable member 190 within the chamber 158. The shelf 174 also can cooperate with the movable member 190 to close the chamber 158 when the assembly 100 is in the preuse state, as further discussed below.

In the illustrated embodiment, a long distal extension 175 of the disinfection chamber 158 can extend distally from the shelf 174. The distal extension 175 has a slightly tapered outer boundary 179 that gradually decreases in cross-sectional area in the distal direction 124. The disinfection chamber 158 can include a support column 168 within a distal region thereof. The support column 168 can be integrally formed with both a base wall 154 and the sidewall 152, and can provide a rigid surface against which the rod 177 can rest. The support column 168 can act as a stop that prevents the rod 177 from moving distally within the chamber 122 past a proximal end of the column 168. In some instances, however, a distal portion of the rod 177 may deform so as to extend distally slightly past the proximal end of the support column 168 when a medical connector is coupled with the cap 108. The support column 168 can reduce the amount of material that might otherwise be used to form the graspable part 137 of the cap 108.

The rod 177, which may also be referred to as a support or a base element, can be configured to provide a base against which the antiseptic reservoir or pad 170 can be compressed so as to force antiseptic therefrom. Accordingly, the rod 177 can be harder, stiffer, or less compliant than the pad 170, and can be configured to compress, under a given force, to a smaller extent than the pad 170 does under the same force. For example, in various embodiments, the rod 177 can be no less than about 2, 3, or 4 times harder than the pad 170.

The rod 177 can be elastically deformable such that compression of the rod 177 from a relaxed orientation gives rise to a restorative force. The rod 177 can naturally return to the relaxed orientation upon removal of the compressive force. The rod 177 can comprise any suitable elastically deformable material. In some embodiments, the rod 177 comprises an elastomeric material, such as silicone. In certain embodiments, the rod 177 comprises a closed configuration (e.g., closed cell foam) or is otherwise nonabsorbent such that little or no antiseptic 133 that is expelled from the pad 170 is received into the rod 177. In other or further embodiments, the rod 177 may comprise a spring (e.g., a compression coil spring).

In the illustrated embodiment, a distal end of the rod 177 seats snugly against the inner surface 166 of the cap 108. The rod 177 may form a fluid-tight seal with the inner surface 166, which may prevent antiseptic 133 that is expelled from the pad 170 from migrating into the distal regions of the disinfecting chamber 158. Rather, the antiseptic 133 can be restrained to the proximal regions of the disinfecting chamber 158 where it can be urged into contact with a male protrusion of a medical connector 1100.

The pad 170 can comprise any suitable material, such as those described above with respect to other pads (including plastically deformable materials, in some instances), and may be elastically or resiliently deformable. In some embodiments, the pad 170 is attached to the rod 177 via any suitable adhesive or other attachment mechanism, although in other embodiments, no such attachment mechanisms are used. For example, the pad 170 and the rod 177 may be maintained in contact with each other due to a slight longitudinal compression of one or more of these components once the cap 104 is assembled (e.g., once the rod 177, the pad 170, and the movable member 190 are positioned between the support column 168 and the shelf 174). Similarly, the pad 170 may be attached to the movable member 190, or it may maintain a substantially fixed orientation relative to the movable member 190 without such attachment due to the resilience of the pad 170 and/or the rod 177, which are in a slightly compressed state.

In FIG. 12, the luer is inserted further into opening, causing the foam component to be squeezed and forcing antiseptic agent out of the foam element. In FIG. 13, the luer is fully inserted into the cap. Generally, in this fully inserted configuration, a fluid-tight seal would be formed if not for the vents 188. In this case, however, antiseptic is able to evaporate through the vents 188 which provide a channel through which the antiseptic may pass. The antiseptic agent is allowed to bathe the exterior surfaces of the luer, but the movable member component 190 inhibits the flow of the antiseptic agent into the luer's cannula.

The vents allow the antiseptic agent to evaporate by providing limited exposure of the cap's chamber to the atmosphere.

For the helical-vent embodiment, the preferred number of vents is 2. The straight-vent embodiments preferably have 4 vents. Alternatively, a straight-vent cap has 8 vents, although both helical-vent and straight-vent caps may have any number of vents that can fit around the circumference of opening, including only a single vent per cap.

Alternative structures, aside from those described above, may be used to vent the chamber to atmosphere after the seal is removed and when the post of the male luer-lock connector is being engaged by the receiving portion. For example, bumps may be located on the inner surface of the cap's receiving portion for keeping open a passage between this inner surface and the outer surface of an inserted male luer tip. This passage allows venting of the cap's chamber to atmosphere. Another alternative structure may include a larger inner diameter of the receiving portion of the cap. In such an arrangement, ribs may be placed on the inner surface of the receiving portion in order to keep the inserted luer tip spaced away from the inner surface of the receiving portion. In a further example, the receiving portion of the cap may include an oval-shaped opening to vent the cap's chamber to atmosphere.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A male-disinfecting cap for applying an antiseptic agent to a medical male luer-lock connector of the type including a post having a lumen through which fluid flows, the cap comprising:
   a receiving portion defining a chamber configured to receive a post of a male luer-lock connector, the chamber comprising an opening and the receiving portion defining an internal surface;
   wherein the receiving portion comprises:
      a tapered surface region disposed adjacent the opening;
      an intermediate region disposed distal to the tapered surface region; and
      a shelf disposed between the tapered surface region and the intermediate region:
   wherein an inner diameter of the intermediate region is larger than an inner diameter of the tapered surface region at a location adjacent to the shelf; and
   a vent disposed on the tapered surface region, the vent extending from the opening and to the intermediate region; and
   an antiseptic fluid disposed in the chamber.

2. The male-disinfection cap of claim 1, wherein the vent comprises a channel.

3. The male-disinfecting cap of claim 2, wherein the vent is parallel to a longitudinal axis of the tapered surface region.

4. The male-disinfecting cap of claim 3, wherein the vent is angled relative to a longitudinal axis of the tapered surface region.

5. The male-disinfecting cap of claim 4, wherein a path of the vent is helical in shape.

6. The male-disinfecting cap of claim 1, wherein the vent is configured to permit evaporation of the antiseptic fluid disposed within the chamber to external atmosphere when the post of the medical male luer-lock connector is disposed within the receiving portion.

7. The male-disinfection cap of claim 6, wherein the vent is configured to control a rate of evaporation of the antiseptic fluid from the chamber to external atmosphere when the post of the male luer-lock connector is disposed within the receiving portion.

8. The male-disinfecting cap of claim 1, wherein the vent is configured to permit flow of the antiseptic fluid from the chamber when the post of the medical male luer-lock connector is disposed within the receiving portion.

9. The male-disinfecting cap of claim 1, wherein the vent is configured to reduce a likelihood of passage of microbes through the vent into the chamber when the post of the medical male luer-lock connector is disposed within the receiving portion.

10. A male-disinfecting cap for applying an antiseptic agent to a medical male luer-lock connector of the type including a post having a lumen through which fluid flows, the cap comprising:
a receiving portion defining a chamber configured to receive a post of a medical male luer-lock connector, the chamber comprising an opening and the receiving portion defining an internal surface;
wherein the receiving portion comprises:
a tapered surface region disposed adjacent the opening;
an intermediate region disposed distal to the tapered surface region; and
a shelf disposed between the tapered surface region and the intermediate region:
wherein an inner diameter of the intermediate region is larger than an inner diameter of the tapered surface region; and
a vent disposed on the tapered surface region, the vent extending from the opening and to the intermediate region;
a pad comprising an antiseptic agent disposed in the chamber; and
a moveable member disposed in the chamber.

11. The male-disinfecting cap of claim 10, wherein the vent comprises a channel.

12. The male disinfection cap of claim 10, wherein the vent is configured to permit evaporation of the antiseptic agent from the chamber to external atmosphere when the post of the medical male luer-lock connector is disposed within the receiving portion.

13. The male-disinfecting cap of claim 10, wherein the moveable member is configured to prevent the antiseptic agent from entering the lumen of the post of the medical male luer-lock connector.

14. A method of disinfecting a medical male luer-lock connector of the type including a post having a lumen through which fluid flows, the method comprising:
coupling a cap to a male luer-lock connector, the cap comprising:
a receiving portion defining a chamber configured to receive a post of the male luer-lock connector, the chamber comprising an opening and the receiving portion defining an internal surface;
wherein the receiving portion comprises:
a tapered surface region disposed adjacent the opening;
an intermediate region disposed distal to the tapered surface region; and
a shelf disposed between the tapered surface region and the intermediate region;
wherein an inner diameter of the intermediate region is larger than an inner diameter of the tapered surface region at a location adjacent to the shelf; and
a vent disposed on the tapered surface region, the vent extending from the opening and to the intermediate region; and
an antiseptic fluid disposed in the chamber; and
wherein coupling the cap comprises moving the cap axially in relation to the medical male luer-lock connector such that the antiseptic agent comes into contact with the post.

15. The method of claim 14, wherein the vent is configured to permit evaporation of the antiseptic agent from the chamber to external atmosphere when the post of the male luer-lock connector is disposed within the receiving portion.

16. The method of claim 14, wherein the vent is configured to control a rate of evaporation of the antiseptic agent from the chamber to external atmosphere when the post of the male luer-lock connector is disposed within the receiving portion.

17. The method of claim 14, wherein the male-disinfecting cap further comprises a moveable member disposed within the receiving portion and configured to prevent flow of the antiseptic agent into the lumen of the post of the medical male luer-lock connector.

* * * * *